(12) United States Patent
Pfeifer

(10) Patent No.: US 6,672,166 B2
(45) Date of Patent: Jan. 6, 2004

(54) ULTRASONIC TRANSDUCER SYSTEM

(75) Inventor: Guenther Pfeifer, Dresden (DE)

(73) Assignee: Sick Engineering GmbH, Ottendorf-Okrilla (DE)

( * ) Notice: Subject to any disclaimer, the term of this patent is extended or adjusted under 35 U.S.C. 154(b) by 0 days.

(21) Appl. No.: 10/316,572

(22) Filed: Dec. 10, 2002

(65) Prior Publication Data

US 2003/0164661 A1 Sep. 4, 2003

(30) Foreign Application Priority Data

Jan. 3, 2002 (EP) .............................. 02004721

(51) Int. Cl.[7] .............................................. G01N 29/24
(52) U.S. Cl. ...................................... 73/632; 73/866.5
(58) Field of Search ...................... 73/632, 644, 861.18, 73/861.25, 861.26, 861.27, 861.28, 861.29, 861.31, 756, 866.5; 310/334, 336

(56) References Cited

U.S. PATENT DOCUMENTS

| | | | | |
|---|---|---|---|---|
| 3,891,869 A | * | 6/1975 | Scarpa ........................ 310/325 |
| 4,063,457 A | * | 12/1977 | Zekulin et al. ............ 73/290 V |
| 4,452,090 A | * | 6/1984 | Kou et al. ................ 73/861.28 |
| 5,275,060 A | | 1/1994 | Lynnworth ................ 73/861.18 |
| 5,437,194 A | * | 8/1995 | Lynnworth ................ 73/861.27 |
| 5,515,733 A | | 5/1996 | Lynnworth ................ 73/861.27 |
| 5,905,693 A | * | 5/1999 | Dubois ......................... 367/173 |
| 6,032,538 A | * | 3/2000 | Rickman et al. ............... 73/756 |
| 6,047,602 A | * | 4/2000 | Lynnworth .................... 73/632 |

FOREIGN PATENT DOCUMENTS

DE 19723488 A1 12/1998

* cited by examiner

*Primary Examiner*—Hezron Williams
*Assistant Examiner*—Rose M. Miller
(74) *Attorney, Agent, or Firm*—Townsend and Townsend and Crew, LLP

(57) ABSTRACT

An ultrasonic transducer system which has an ultrasound transducer and a filter supporting the transducer. To suppress the transmission of ultrasound signals through a housing of the ultrasound transducer arrangement, the filter is provided with a vibration plate for emitting ultrasound waves and is coupled to a deflecting segment which converts radial movements of a first section of the filter into torsional movements of a second section of the filter.

20 Claims, 5 Drawing Sheets

ULTRASONIC TRANSDUCER SYSTEM

BACKGROUND OF THE INVENTION

This invention relates to ultrasonic transducer systems which have an ultrasound transducer supported by a filter.

U.S. Pat. No. 5,275,060 discloses such an ultrasonic transducer system. Ultrasound transducers can be used in gas meters, for example. Pairs of ultrasound transducers define a measuring path which lies at an angle other than a right angle to the longitudinal axis of the fluid flow. Measurements make use of the difference in transition times between two ultrasonic signals which have a component in the flow direction and another component against the flow direction. The flow velocity can be calculated from the measured difference in the transition time.

The piezo crystal which generates ultrasound waves in known ultrasonic transducer systems is mounted to the measuring instrument via an acoustic filter. The purpose for the acoustic filter is to suppress inductive disturbances, or cross-talk, generated by transmissions between an ultrasonic emitter and an ultrasonic receiver. Such filters have a cylindrical shape and a multitude of alternatingly arranged sections of greater and lesser wall thickness to provide segments of higher and lower impedance relative to axially translating motions. This arrangement at least reduces the effect of cross-talk through the housing on the ultrasonic signals.

Since ultrasonic signals transmitted through the housing have significantly shorter transit times than signals which propagate through the fluid medium to be measured, cross-talk or inductive disturbances can be a source of significant interference.

However, this known acoustic filter is primarily effective for dampening axial forces. Ultrasound transducers attached to circular plates for uncoupling ultrasound transmissions through solid bodies primarily subject the filter to torsional moments which, amongst others, lead to radial strain waves and radial oscillations in the components, which subjects the ultrasonic signals to cross-talk. The known acoustic filter of U.S. Pat. No. 5,275,060 provides insufficient dampening of such waves.

SUMMARY OF THE INVENTION

In view of this state of the art, it is an object of the invention to provide an improved ultrasonic transducer system which significantly improves the suppression of cross-talk through the housing, and particularly cross-talk caused by radial strain waves and oscillations.

According to the invention, the filter of the ultrasonic transducer system is coupled to a deflection or vibration plate of the ultrasound transducer from which ultrasound waves radiate. The filter has a deflecting segment which transforms a radial deflection of a first section of the filter into a rotational or torsional deflection of a second section of the filter. The arrangement provided by the present invention has the particular advantage that by combining radial vibrations of the first section and torsional vibrations of the second section via the deflection plate, an optimal filtering of the ultrasonic signals is attained. This effectively eliminates or at least greatly reduces the transmission of cross-talk signals from the ultrasound transducer into the housing of the measuring instrument.

The deflecting segment converts radial deflections of the first section into torsional deflections of the second section. By appropriately dimensioning the subsystem consisting of the two sections and the deflecting segment, a virtually motionless state of the second section is attained over a frequency range that includes the operational frequency range of the ultrasound transducer. Thus, the second section is subjected to substantially no torsional vibrations. An optimal filtration effect is attained in this manner.

The filter is preferably coupled to the rim of a pliant vibration plate. The ultrasound generating component causes the deflection of a mid-portion of the bending plate. In this manner, the filter is subjected to only small axial forces. The vibration plate and the first section of the filter are preferably connected by soldering or welding the first section directly to the rim of the vibration plate.

The ultrasonic transducer system of the invention is preferably of a simple, rotationally symmetric construction.

In a similarly simple manner, the deflecting segment preferably connects the longitudinal end of the first section with an inner side of the second section so that radial movements of the longitudinal end of the first section are transformed into torsional movements of the second section.

The deflecting section is conveniently and preferably a simple disc which has a 90° bend.

In an easily manufactured embodiment of the invention, the first section is formed as a tubular casing with a wall thickness that preferably changes in the longitudinal direction and which preferably increases in the direction of the second section. This suppresses resonances caused by the thickness of the tubular casing, which can be the source of cross-talk and reduce the available band width of the filter.

The second section is preferably manufactured as a torsion ring.

To facilitate the radiation of ultrasound waves from the mid-portion of the vibration plate while minimizing the transmission of axial forces to the filter, the vibration plate preferably has a mass ring at its periphery.

For attaching the ultrasonic transducer system to a housing of a measuring system, an attachment flange is provided which secures the filter and therewith the ultrasound transducer.

It is particularly advantageous when the filter with its two sections and the deflecting segment are of a one-piece construction by assembling the components into a single unit.

The filter and its components should be dimensioned so that no resonances are generated over the operational frequency band width of the ultrasound transducer. For example, the first torsional resonance of the torsion ring and its radial resonance should lie below the operational band width of the filter.

An optimal effectiveness of the filter results from dimensioning the components so that the second section is preferably free of vibrations over the operational frequency band due to its rotational mass so that essentially no vibrations are transferred to the housings of the measuring system.

The length of the first section is selected so that axial resonances are outside the operational frequency band width.

Exemplary embodiments of the invention are described with reference to the drawings.

DESCRIPTION OF THE PREFERRED EMBODIMENTS

Figure 1:
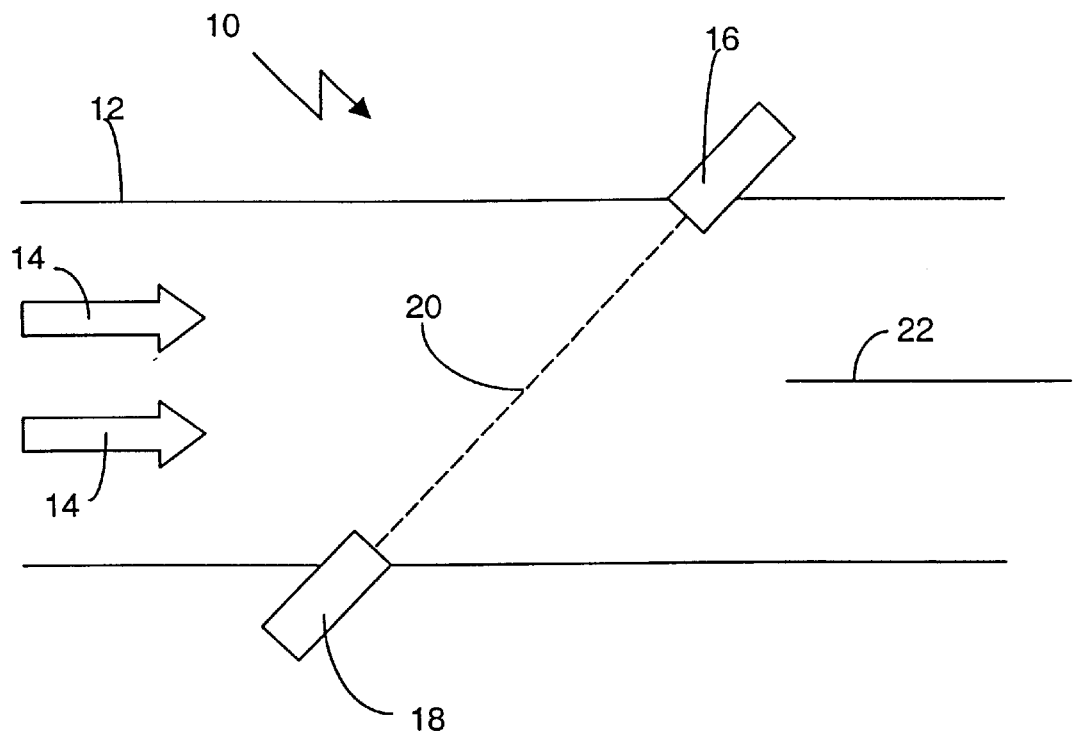
FIG. 1 illustrates a measuring system using an ultrasound transducer arrangement according to the present invention.

FIG. 1 illustrates the measurement principle employed by the present invention as used, for example, in a measuring system installed in an ultrasonic gas meter. Gas flows along a pipe 12 in a flow direction 14. Ultrasonic transducer arrangements 16 and 18 define a measurement path 20 in pipe 12. Ultrasonic transducer arrangements 16, 18 include ultrasound transducers capable of converting electrical signals into ultrasound and vice versa for emitting and receiving ultrasound. Measurement path 20 forms an angle other than 90° with a longitudinal axis 22 of pipe 12. As a result, ultrasound signals are directed in opposite directions along measuring path 20 so that, due to gas flow 14, differences in the respective transit times arise. The flow velocity, and therewith the volumetric flow-through of fluid media such as gases, can be determined from this difference.

The ultrasonic signals propagate not only along measuring path 20, they also propagate through the housing of measurement arrangement 10, that is, via ultrasonic transducer arrangements 16 and 18 and through the massive pipe 12. Ultrasonic signals which are transmitted through the housing travel at a much higher speed than ultrasound signals through the gas flow along measurement path 20. They therefore interfere with the measurements that are being taken.

Ultrasonic transducer arrangements 16 and 18 constructed in accordance with the present invention reduce ultrasonic transmissions through solids such as the housing or the pipe.

Figure 2:
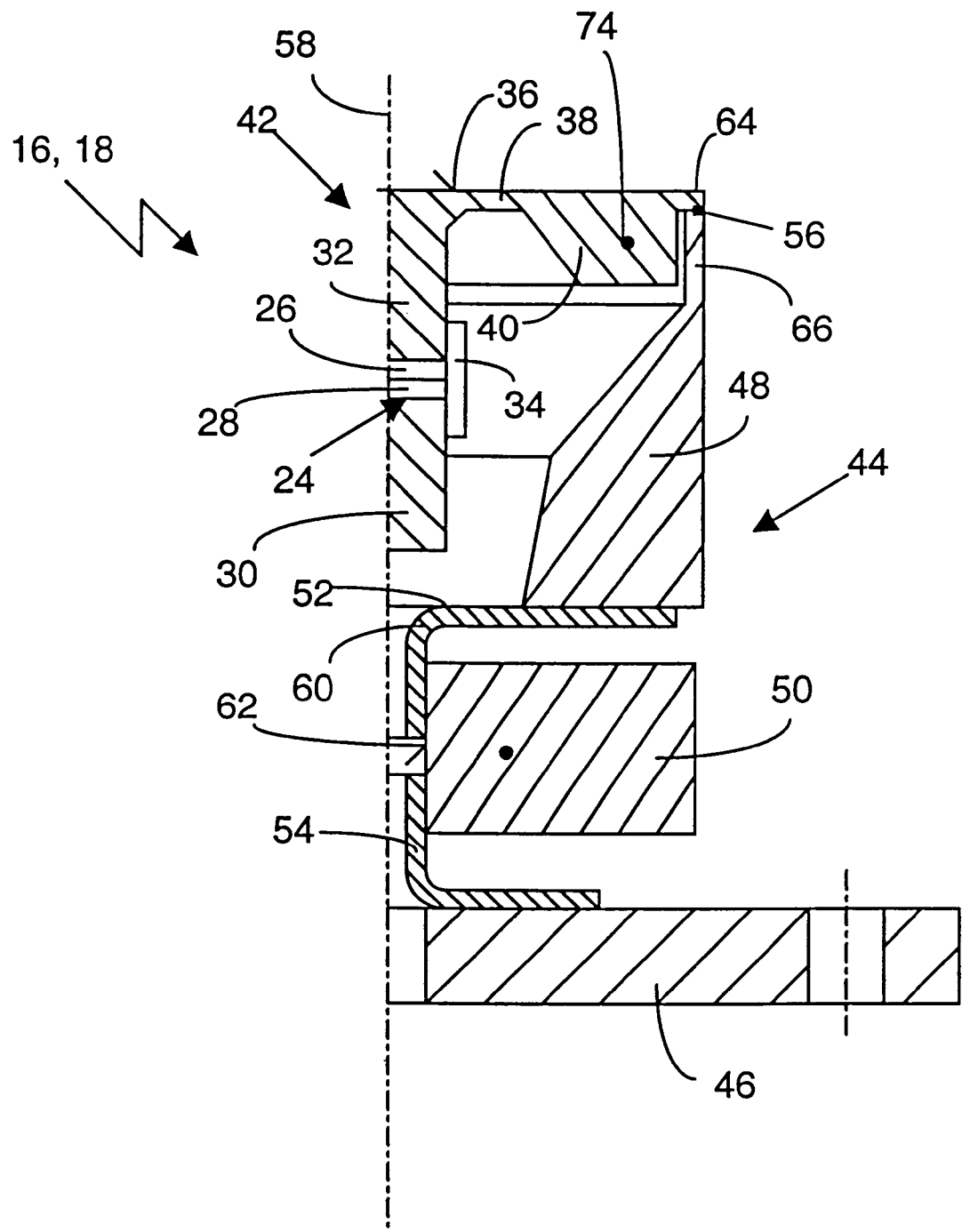
FIG. 2 is a partial, cross-sectional view of an embodiment of the ultrasonic transducer system of the present invention.

FIG. 2 illustrates one of ultrasonic transducer arrangements 16, 18 in cross-section. It includes an ultrasound transducer 42 that supports an ultrasound filter 44 secured to a mounting flange 46.

Ultrasound transducer 42 has an element 24 that generates ultrasound and is made of two piezo ceramics 26, 28 that are connected by electric leads (not shown). Piezoelectric element 24 is secured between two tension members 30 and 32. Tension member 30 is made of heavy metal, for example steel, and the other member is made from a light metal, preferably titanium, aluminum or magnesium. The two tensioning members 30, 32 are connected by a tensioner 34 which permits the tensioning of the piezoelectric element 24 between the tensioning members. A free face 36 of tensioning member 22 is used as an emitting and/or receiving surface from which ultrasonic signals can be emitted and/or which can receive ultrasonic signals. To enlarge face 36 and decouple the face from axially acting vibration forces, the face is defined by a vibration plate 38. In the vicinity of its rim 64, vibration plate 38 has a mass ring 40. The piezoelectric element, together with tensioning members 30 and 32 and the associated vibration plate 38 and mass ring 40 as well as tensioner 34, form ultrasound transducer 42.

Filter 44 includes first and second sections 48, 50, which are connected by deflecting segment 52, and a mounting member 54.

The first section 48 of filter 44 is formed as a tubular casing or pipe. It includes the transducer 42 and for simplicity is referred to as tubular casing 42. The upper end of tubular casing 48 (as seen in FIG. 2) is connected to rim 64 of vibration plate 38 of the ultrasound transducer 42, preferably by a soldered or welded seam 56. The wall thickness of tubular casing 48 changes in the direction of longitudinal axis 58. In the illustrated embodiment, the wall thickness increases in the direction towards second section 50.

Deflecting segment 52 is attached to the end of second section 50 which faces first section 48 and preferably is formed as a disc that includes a 90° bend 60.

The second section 50 is a massive, short ring and for simplicity is referred to as torsion ring 50. The deflecting segment 52 is secured to an inner surface 62 of the ring defined by the deflecting segment 52. Mounting member 54 is attached to inner surface 62 of the ring-shaped second section.

Although filter 44 is illustrated in the drawing figures as being made of multiple parts, it is preferred that it is of a one-piece construction comprising filter 44 and its tubular casing 48, deflecting segment 52, torsion ring 50 and mounting member 54 assembled into a single unit.

In the following, various vibration states of the ultrasonic transducer arrangements 16, 18 of the present invention, and in particular of filter 44, and the manner in which the filter operates are described in more detail.

Figure 3:
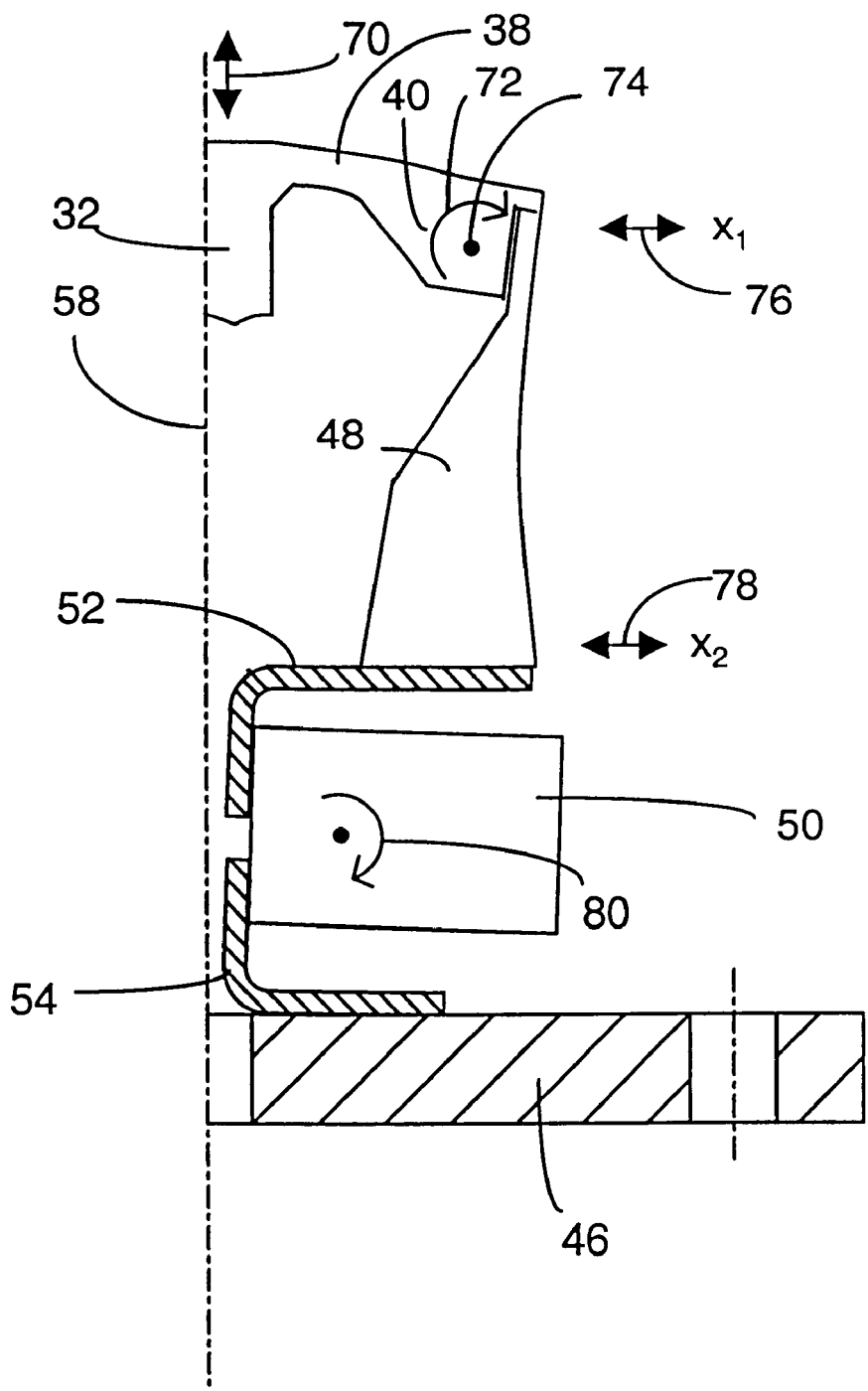
FIG. 3 corresponds to FIG. 2 and schematically and in exaggerated form illustrates a vibration state.
Figure 4:
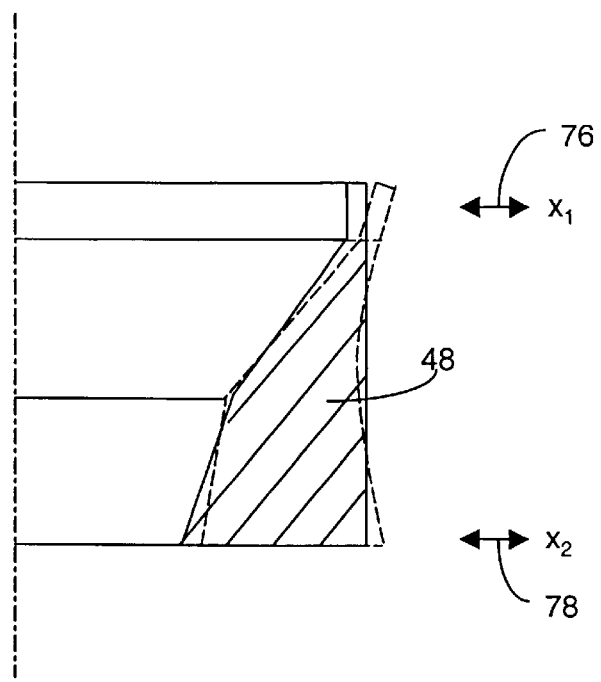
FIG. 4 illustrates a vibration movement in the first section.
Figure 5:
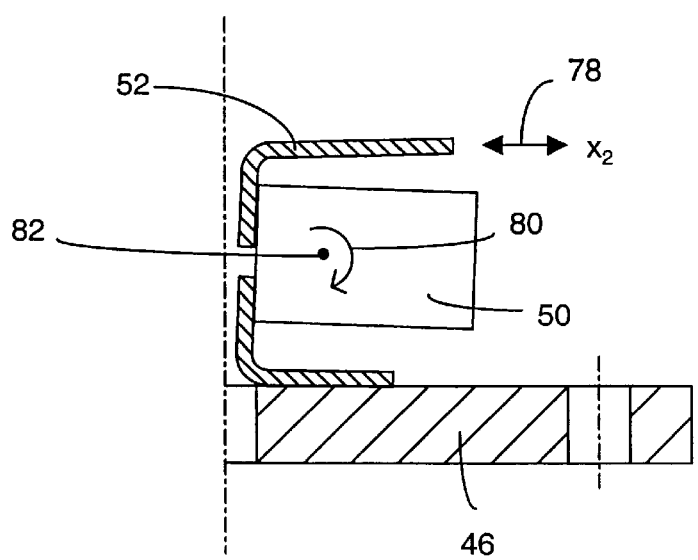
FIG. 5 illustrates a vibration movement in the second section.

FIGS. 3, 4 and 5 schematically illustrate in an exaggerated manner possible vibrations encountered by the ultrasonic transducer arrangement and its individual components. Piezoelectric element 24 generates vibrations which are transmitted to the mid-portion of a circular vibration plate 38 via tensioning member 32 so that the vibration plate is subjected to deflections as illustrated by double arrow 70 in FIG. 3. The vibrating plate 38 generates ultrasonic waves or signals in the longitudinal direction 58. Conversely, incoming ultrasonic signals traveling in longitudinal direction 58 are received by and cause vibrations (double arrow 70) in the vibration plate and are converted into electric signals by piezoelectric element 24.

The vibrating tension member 32 transmits a radially symmetric torsion moment via vibration plate 38 to mass ring 40. This causes torsional movements of the mass ring in the direction of arrow 72 (FIG. 3) about a circular torsion center 74. In view of its translational mass, the mass ring impedes axial movements and, due to its stiffness in a radial direction, radial movements of vibration plate 38. Manufacturing problems make it difficult or impossible to attain the desired degree of rotational and radial stiffness for the mass ring. As a result, torsional movements 72 and radial movements act on the resilient mass ring 40.

The solder connection necessarily converts a torque applied to mass ring 40 into a torsional moment acting on the upper end of tubular casing 48. If the tubular casing 48 were free, radial strain waves would propagate axially along the tubular casing and thereby transfer sound waves traveling through a solid body to mounting flange 46 and therewith to the housing of the measuring instrument. In such a case, the tubular casing 48 would constitute a short radial strain wave conductor. Such strain waves cannot be eliminated because the inside diameter of the tubular casing cannot be made as small as desired since the ultrasound transducers are arranged on its inside.

It is not possible to construct the tubular casing 48 as a pliant radial bending wave conductor which could absorb such waves in order to keep the initial torsional moments small because the system must be capable of withstanding the high surrounding pressures to which it is subjected.

Deflecting segment 52 is connected to the lower end of tubular casing 48 and forms a radially and axially effective spring zone. The lower end of tubular casing 48 is subjected to periodic radial movements $x_2$ as is illustrated by double arrow 78 (FIG. 3).

Deflecting segment 52 converts the radial movements $x_2$ at the lower end of tubular casing 48 into torque acting on torsion ring 50 as is schematically illustrated in FIG. 5. As a result, torsion ring 50 is subjected to torsional movements in the direction of arrow 80 about an annular torsion center 82.

To enable torsional movements 80, mounting member 54 and deflecting segment 52 are secured to the inside surface 62 of torsion ring 50.

The objective of filter 44 is to eliminate sound transmissions through solid bodies over the operational frequency range of ultrasound transducer 42. To attain an optimal effectiveness of filter 44, the resonances of the individual components of the filter should be outside the operational frequency range. These resonances include thickness resonances, radial resonances and torsional resonances of mass ring 40, for example, as well as longitudinal resonances and the like. A proper dimensioning of the individual components makes it possible to provide them with resonances which lie in non-interfering frequency ranges, i.e. outside the operational frequency range of the system.

The vibration system formed by deflecting segment 52 and torsion ring 50 should be tuned in regards to their torsion and radial resonances so that the torsion ring is in a substantially motionless state over the operational frequency range. This is attained by carefully selecting the inner and outer diameters as well as the height of the torsion ring in combination with the resiliency of the deflection zone. The first torsion resonance should be below the operational frequency range of the transducer so that the total torsional mass of torsion ring 50 opposes movement. In addition, the first radial resonance should remain outside the operational frequency range. In such an event, the torsion ring 50 is subjected to virtually no vibrational movements over the operational frequency range, which makes filter 44 optimally effective.

Figure 6:
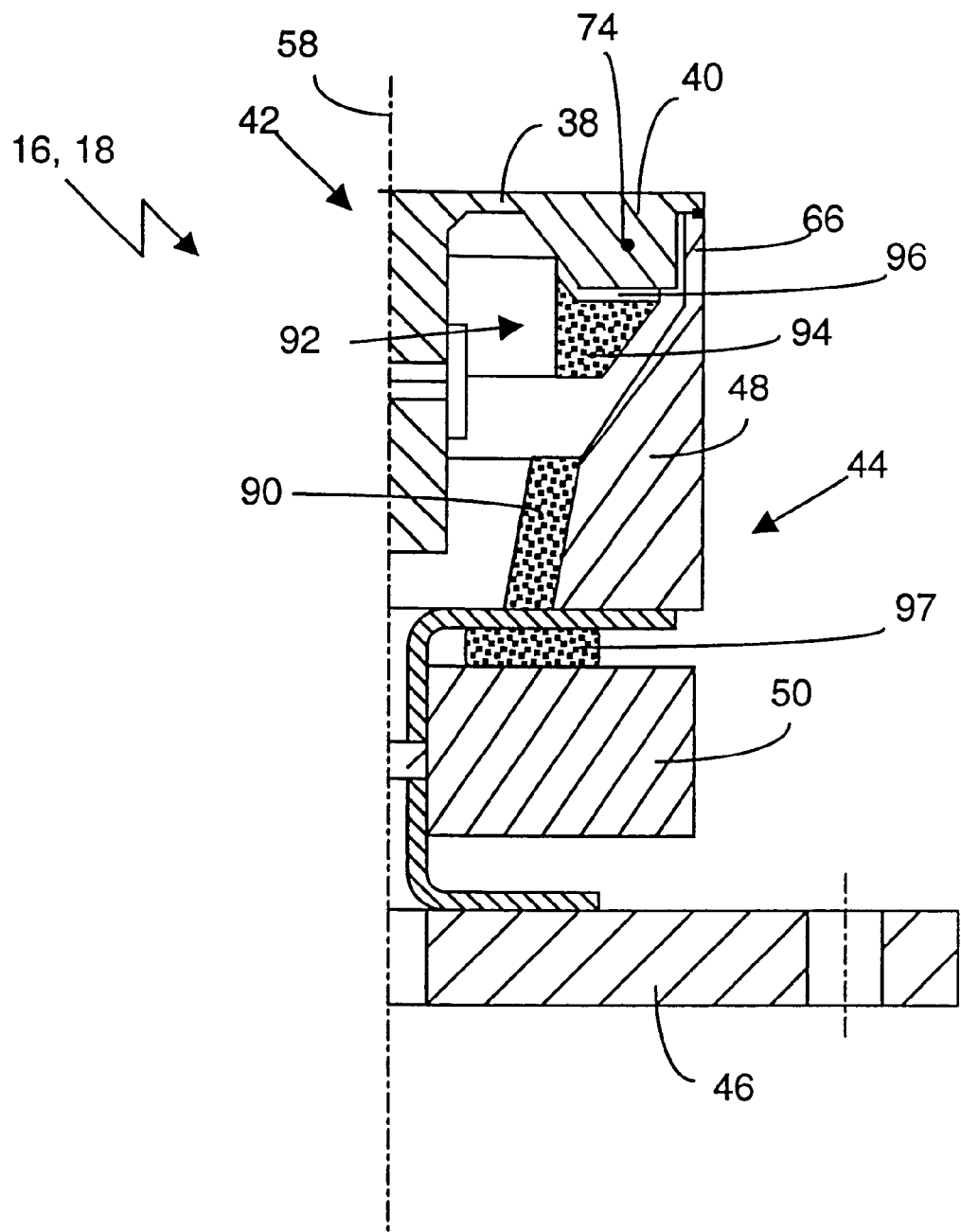
FIG. 6 shows another embodiment of the ultrasonic transducer system of the present invention.

The vibration energy transmitted to filter 44 by torsional moments of vibration plate 38 is dissipated in tubular jacket 48. To enhance this process, the embodiment of the invention illustrated in FIG. 6 provides a dampening layer 90 which is preferably applied to a lower portion of the interior wall of tubular jacket 48. In this manner, strain waves and radial resonances of the tubular jacket 48 caused by a broad band excitation below the operational frequency range are dampened. This provides filtering over a wider range.

To further enhance the effectiveness of the filter, another dampening layer 92 can be applied to mass ring 40 in the form of a body 94 made of plastic or metal. It is secured to the mass ring with an energy absorbing bonding layer 96.

To avoid a slow decrease in vibrations in the event torsion ring 50 has been excited, a further dampening layer 97 can be placed between deflecting segment 52 and torsion ring 50. Instead of dampening layer 97, a dampening ring can be used.

These further provisions help to dampen all partial resonances which act on mass ring 40 and tubular casing 48.

What is claimed is:

1. An ultrasonic transducer system comprising an ultrasound transducer and a filter supporting the ultrasound transducer, the filter including a vibration plate operatively coupled to the ultrasound transducer for emitting ultrasonic signals generated by the ultrasound transducer, a first section, a second section, and a deflecting segment which converts movements of the first section in a radial direction into torsional movements of the second section.

2. An ultrasonic transducer system according to claim 1 wherein a mid-portion of the vibration plate is deflected when subjected to ultrasound generated by an ultrasound generating element, and wherein the filter is coupled to a rim of the vibration plate.

3. An ultrasonic transducer system according to claim 1 wherein the deflecting segment is coupled to an end of the first section and an inner side of the second section.

4. An ultrasonic transducer system according to claim 1 wherein the deflecting segment comprises a disc.

5. An ultrasonic transducer system according to claim 4 wherein the deflecting segment includes a 90° bend.

6. An ultrasonic transducer system according to claim 1 wherein the filter is rotationally symmetric.

7. An ultrasonic transducer system according to claim 1 wherein the first section comprises a tubular casing.

8. An ultrasonic transducer system according to claim 1 wherein the second section comprises a torsion ring.

9. An ultrasonic transducer system according to claim 1 wherein the vibration plate comprises a mass ring at its periphery.

10. An ultrasonic transducer system according to claim 1 including a mounting flange, and wherein the filter is secured to the mounting flange.

11. An ultrasonic transducer system according to claim 1 wherein the filter comprises a one-piece construction.

12. An ultrasonic transducer system according to claim 1 wherein all resonances of the filter and individual components thereof are outside an operational frequency band width of the ultrasound transducer.

13. An ultrasonic transducer system according to claim 1 wherein the filter and individual components thereof are dimensioned so that the second segment is substantially motionless over an operational frequency band width of the ultrasound transducer.

14. An ultrasonic transducer system according to claim 7 wherein the tubular casing has a wall thickness which increases in a direction towards the second section.

15. An ultrasonic transducer system according to claim 1 wherein the first section has a length so that an axial resonance thereof is outside an operational frequency band width of the ultrasound transducer.

16. An ultrasonic transducer system according to claim 1 wherein the first section includes a dampening layer.

17. An ultrasonic transducer system according to claim 9 including a dampening layer applied to the mass ring.

18. An ultrasonic transducer system according to claim 1 including a dampening layer between opposing ends of the first section and the second section.

19. An ultrasonic transducer system according to claim 1 including a dampening ring arranged between opposing ends of the first and second sections.

20. An ultrasonic transducer according to claim 17 including a layer of a bonding agent between the dampening layer and the mass ring.

* * * * *